United States Patent
Hellmers et al.

(10) Patent No.: US 10,626,391 B2
(45) Date of Patent: Apr. 21, 2020

(54) GRANULES COMPRISING ISOMALTULOSE SYNTHASE

(71) Applicant: Evonik Operations GmbH, Essen (DE)

(72) Inventors: Frank Hellmers, Muenster (DE); Thomas Hueller, Marl (DE); Thomas Dassinger, Babenhausen (DE); Oliver Thum, Ratingen (DE)

(73) Assignee: Evonik Operations GmbH, Essen (DE)

( * ) Notice: Subject to any disclaimer, the term of this patent is extended or adjusted under 35 U.S.C. 154(b) by 184 days.

(21) Appl. No.: 15/123,514

(22) PCT Filed: Mar. 3, 2015

(86) PCT No.: PCT/EP2015/054361
§ 371 (c)(1),
(2) Date: Sep. 2, 2016

(87) PCT Pub. No.: WO2015/132230
PCT Pub. Date: Sep. 11, 2015

(65) Prior Publication Data
US 2017/0002342 A1    Jan. 5, 2017

(30) Foreign Application Priority Data

Mar. 5, 2014   (DE) ........................ 10 2014 203 964

(51) Int. Cl.
| | | |
|---|---|---|
| C12N 9/98 | (2006.01) | |
| C12N 9/90 | (2006.01) | |
| C08L 33/12 | (2006.01) | |
| C08L 33/04 | (2006.01) | |
| C12N 11/16 | (2006.01) | |

(52) U.S. Cl.
CPC ............... *C12N 9/98* (2013.01); *C08L 33/04* (2013.01); *C08L 33/12* (2013.01); *C12N 9/90* (2013.01); *C12N 11/16* (2013.01); *C12Y 504/99011* (2013.01)

(58) Field of Classification Search
CPC ........... C12N 9/90; C12N 9/98; C08F 220/14; C12Y 504/99011
USPC ................. 435/174, 210; 530/445; 536/23.2
See application file for complete search history.

(56) References Cited

U.S. PATENT DOCUMENTS

| | | |
|---|---|---|
| 5,972,668 A | 10/1999 | Georg et al. |
| 8,404,470 B2 | 3/2013 | Thum et al. |
| 8,486,677 B2 | 7/2013 | Thum et al. |
| 8,796,000 B2 | 8/2014 | Thum et al. |
| 9,600,773 B2 | 3/2017 | Dhurandhar et al. |

FOREIGN PATENT DOCUMENTS

| | | |
|---|---|---|
| CN | 1466092 A | 1/2004 |
| WO | WO 96/00773 A1 | 1/1996 |

OTHER PUBLICATIONS

Schantz et al Langmuir 2007, 23 pp. 3590-3602.*
Du et al. Macromole. 2004, 37, pp. 803-812.*
U.S. Appl. No. 14/118,078, filed Nov. 15, 2013, 2014/0086997 A1, Kathrin Nollenberger et al.
U.S. Appl. No. 14/378,565, filed Aug. 13, 2014, 2015/0024106 A1, Thomas Hueller et al.
International Search report dated Apr. 30, 2015 in PCT/EP2015/054361.
K. Piskin, el al. "Radiopolymerized Mixture of Acrylic Acid, Methyl Methacrylate, and Polyethylene Glycol as an Enzyme Support System" The Humana Press Inc. Applied Biochemistry and Biotechnology, XP035178029, vol. 10, No. 1-3, 1984, pp. 73-79.
Combined Office Action and Search Report issued Feb. 29, 2019 in Chinese Patent Application No. 201580011914.0, 13 pages (with English translation).
Yan, B. et al. "Development and Application of Materials Used as Cell Immobilization Carriers" Guangdong Chemical Industry, vol. 37. No. 4, 2010, pp. 11, 12. And 39 (with English abstract).

* cited by examiner

*Primary Examiner* — Robert B Mondesi
*Assistant Examiner* — Mohammad Y Meah
(74) *Attorney, Agent, or Firm* — Oblon, McClelland, Maier & Neustadt, L.L.P.

(57) ABSTRACT

The invention provides granules comprising
A) at least one enzyme selected from at least one of the groups selected from transferases of EC 2, hydrolases of EC 3, lyases of EC 4 and isomerases of EC 5,
B) at least one polymer selected from $C_1$-$C_{10}$-alkyl acrylate polymer, $C_1$-$C_{10}$-alkyl methacrylate polymer and $C_1$-$C_{10}$-alkyl acrylate-$C_1$-$C_{10}$-alkyl methacrylate copolymer, preferably $C_1$-$C_{10}$-alkyl acrylate-$C_1$-$C_{10}$-alkyl methacrylate copolymer and
C) at least one inorganic carrier material.

15 Claims, 4 Drawing Sheets

GRANULES COMPRISING ISOMALTULOSE SYNTHASE

FIELD OF THE INVENTION

Figure 1:
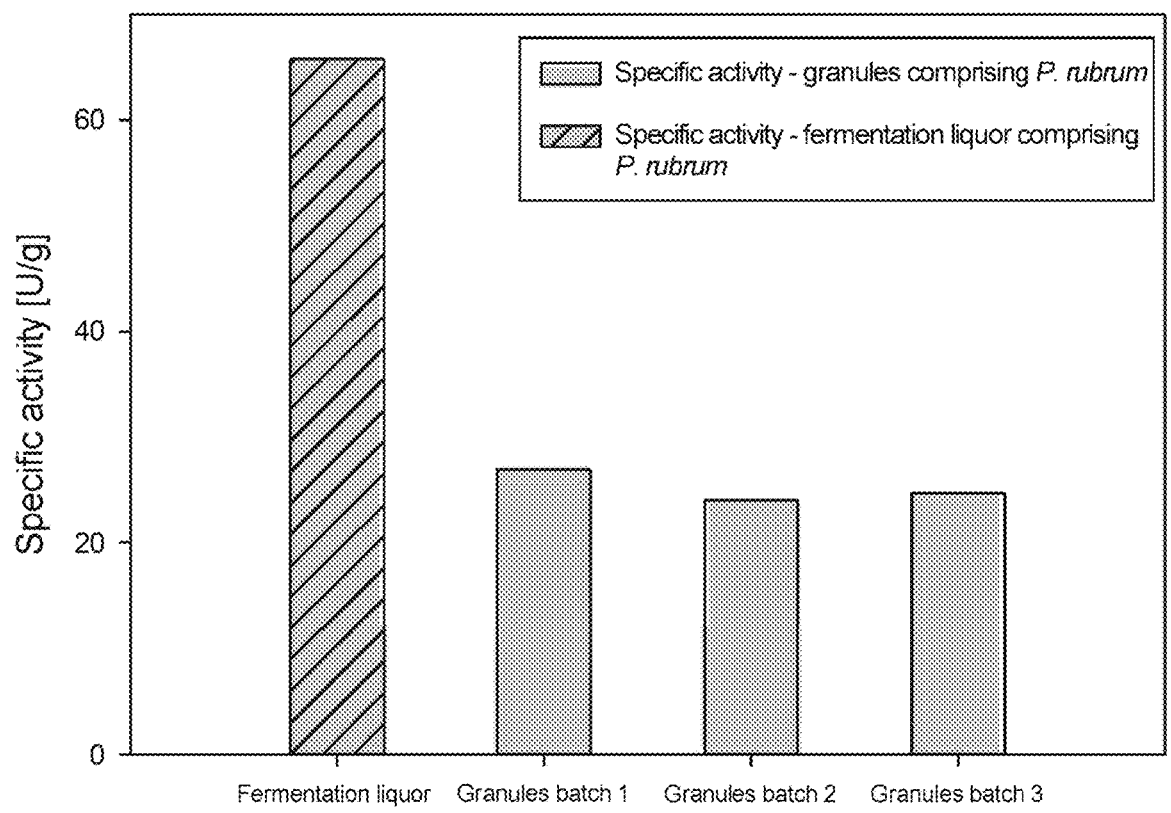

The invention provides granules comprising
A) at least one enzyme selected from at least one of the groups selected from transferases of EC 2, hydrolases of EC 3, lyases of EC 4 and isomerases of EC 5,
B) at least one polymer selected from $C_1$-$C_{10}$-alkyl acrylate polymer. $C_1$-$C_{10}$-alkyl methacrylate polymer and $C_1$-$C_{10}$-alkyl acrylate-$C_1$-$C_{10}$-alkyl methacrylate copolymer, preferably $C_1$-$C_{10}$-alkyl acrylate-$C_1$-$C_{10}$-alkyl methacrylate copolymer and
C) at least one inorganic carrier material.

STATE OF THE ART

The isomerization of sucrose with the help of immobilized whole cells, cell extracts or purified enzymes is described widely in the literature (Südzucker AG, DE3038219C2; Mitsui Sugar Co., U.S. Pat. No. 4,386,158). By way of example, the enzymatic reaction to isomaltulose and also the byproducts trehalulose, glucose, fructose and small fractions of oligosaccharides is considered below. The use of active free cells leads to increased product purification costs and lower yields (Landbauforschung Völkenrode (2002) SH 241:75-80). For this reason, an immobilization of the biocatalytically active material usually takes place.

Virtually all known immobilization methods are described for the biocatalytic isomerization of sucrose, such as, for example, the adsorptive binding of biocatalytically active material to ion exchangers (Danisco AS, EP0915986B1), the inclusion in various synthetic polymers (Bayer AG, DE3416140A1) or natural polymers (Südzucker AG, DE3038219C2; Mitsui Sugar Co., U.S. Pat. No. 4,386,158). An overview of customary immobilization methods is given in the literature (Topics in Current Chemistry, Vol. 200:95-126).

For the stated process, the inclusion of intact cells or non-purified fermentation liquors in alginate polymers in particular has become established (Südzucker AG, DE3038219C2; Mitsui Sugar Co., U.S. Pat. No. 4,386,158). The immobilizates are produced by means of a dropwise addition of a suspension of cell material or purified enzymes and an alginate solution to a solution which comprises calcium chloride ions (Bioresource Technology (2009), Vol. 100:4252-4256). A disadvantage of this is that the immobilizates produced in this way consist to a major part of water. For this reason, storage or keeping can only take place under damp conditions since drying leads to irreversible damage in the immobilizate structure. Damp keeping promotes contamination with foreign germs which must not exceed the stipulated limits according to Regulation (EG) No. 178/2002 concerning maximum contents of certain contaminations in foods. Foreign contamination is associated with increased water activity ($a_w$ value>0.65) (s. Schimmelpilze: Vorkommen, Gesundheitsgefahren, Schutzmassnahmen. Wolfgang Mücke, Christa Lemmen. 2004. Ecomed Medizin, Verlagsgruppe Hüthig Jehle Rehm GmbH). Moreover, alginate immobilizates have proven to be unstable, especially under the influence of even small cation concentrations, as are present e.g. in buffered solutions (Focus on Biotechnology, Vol. 8B:375-405). For this reason, a stabilization by additional crosslinking is usually achieved using glutaraldehyde and polyethyleneimine (Mitsui Sugar Co., U.S. Pat. No. 4,386,158; Bioresource Technology (2009), Vol. 100:4252-4256). A disadvantage here is in particular a reduction in the enzyme activity as a result of using glutaraldehyde (Process Biochemistry (2006) Vol. 41:2035-2040). Also disadvantageous are increased disposal costs (hazardous waste according to Waste Classification Ordinance (AVV) (as at Oct. 12, 2001)) as a result of using the crosslinkers. The production of dry-stable, biocatalytically active granules is described widely in the literature. Lipid Sci. Technol.—2003—Vol. 105.—pp. 318-321 describes a process for the immobilization of *Candida antarctica* Lipase B for ester production, although this is not stable in aqueous processes on account of the choice of binder (maltodextrin). Novo Nordisk AS, WO9522606 describes the use of the binder polyvinylpyrrolidone (Kollidon K25, BASF) for enzyme granulation. However, this combination is not stable in aqueous solutions.

Glatt Ingenieurtechnik GmbH, EP1595942A1, describes a preparation containing microorganisms which is subsequently provided with a protective coating, for example by shellac, for the purposes of stabilization. The purpose of this coating process is to protect the preparations against media such as e.g. water or atmospheric oxygen. Consequently, such preparations are per se unsuitable for use in biotransformations where an intensive mass transfer between medium and biocatalyst must be achieved.

The object of the invention is therefore the provision of new types of enzyme preparations and processes for producing the same which overcome at least one of the aforementioned disadvantages of the prior art. In particular, the object is the production of storage-stable, moisture-insensitive enzyme preparations with a high apparent enzyme activity and improved mechanical stability.

DESCRIPTION OF THE INVENTION

Surprisingly, it has been found that by using a mixture of an inorganic carrier material with a preferably hydrophilic surface such as e.g. precipitated silicas, a $C_1$-$C_{10}$-alkyl (meth)acrylate (co)polymer, and enzymes, preparations with a high biocatalytic activity can be produced using known granulation processes such as extrusion.

Consequently, the invention provides granules comprising
A) at least one enzyme selected from at least one of the groups selected from transferases of EC 2, hydrolases of EC 3, lyases of EC 4 and isomerases of EC 5,
B) at least one polymer selected from C1-C10-alkyl acrylate polymer, C1-C10-alkyl methacrylate polymer and C1-C10-alkyl acrylate-C1-C10-alkyl methacrylate copolymer, preferably C1-C10-alkyl acrylate-C1-C10-alkyl methacrylate copolymer and
C) at least one inorganic carrier material.

The present invention further provides a process for producing the granules according to the invention.

One advantage of the present invention is that the granules are drying-stable.

A further advantage of the present invention is that the granules are storage-stable.

A yet further advantage of the present invention is that the granules can be kept with low contamination.

It is a further advantage of the present invention that the granules are mechanically stable.

A yet further advantage of the present invention is that the granules require no hazardous substances for additional crosslinking such as glutaraldehyde or polyethyleneimine.

It is a further advantage of the present invention that the granules have a high stability even in aqueous media.

The present invention is described hereinafter by way of example, without any intention of limiting the invention to these illustrative embodiments.

The accession numbers listed in connection with the present invention correspond to the protein bank database entries of the NCBI with a date of 1 Oct. 2013; generally, in the present case, the version number of the entry is identified by ".number" such as, for example, "0.1".

Where documents are cited in the context of the present description, it is intended that their content fully form part of the disclosure content of the present invention.

Unless otherwise stated, all percentages (%) given are percentages by weight.

The granules according to the invention are preferably solid.

They advantageously have a half-value particle size d50 [μm] in the range from 100 to 2000 μm, in particular in the range from 200 to 1500 μm and specifically in the range from 700 to 1300 μm. According to the definition, the d50 [μm] value marks the point at which the half investigated particle amount is greater or lesser. Furthermore, the d10 and the d90 values give the range in which 10% or 90%, respectively, are less than or equal to this particle size. The half-value particle size d50 [μm], and also the d10 [μm] and the d90 [μm] value of the particle collective are ascertained here with the help of a Camsizer® from Retsch (Haan, Germany) via the method of dynamic image analysis with the choice of standard settings (ISO 13322-2:2006).

The measurement method used produces a detailed particle size analysis of the overall particle collective, which is shown as a distribution density function. In the distribution density function, the d50 value is taken to be the abscissa value of the greatest maximum.

Preferably, particle collectives of a narrow particle size distribution are to be selected. These are characterized in that the d10 [μm] value of the particle collective is not less than 50% and the d90 [μm] is not greater than 150% of the half-value particle size d50 [μm].

The granules according to the invention very particularly preferably comprise at least one enzyme selected from at least one of the groups selected from glycosyltransferases of EC 2.4, fructan β-fructosidases of EC 3.2.1.80, β-galactosidase of EC 3.2.1.23, invertases of EC 3.2.1.26, aspartate β-decarboxylase of EC 4.1.1.11, fumarate hydratases of EC 4.2.1.2, nitrile hydratases of EC 4.2.1.84, aspartases of EC 4.3.1.1, xylose isomerases of EC 5.3.1.5 and isomaltulose synthases of EC 5.4.99.11.

The granules according to the invention very particularly preferably comprise at least one isomaltulose synthase of EC 5.4.99.11.

Granules preferred according to the invention are characterized in that the isomaltulose synthase is selected from the group of the proteins YP_002235756.1, WP_006325065.1, WP_012540141.1, WP_004157672.1, CCO82510.1, CCO82509.1, CCO78715.1, EKF64560.1, AAP57084.1, AAP57083.1, ACI12079.1 and ACF42098.1, and also proteins with a polypeptide sequence in which up to 60%, preferably up to 25%, particularly preferably up to 15%, in particular up to 10, 9, 8, 7, 6, 5, 4, 3, 2, 1% of the amino acid radicals are changed compared to the aforementioned reference sequences by deletion, insertion, substitution or a combination thereof, and which also have at least 50%, preferably 65%, particularly preferably 80%, in particular more than 90%, of the activity of the protein with the corresponding, aforementioned reference sequence, where 100% activity of the reference protein is understood as meaning the material amount of sucrose reacted per time unit, based on the amount of reference enzyme used, to the corresponding isomaltulose. The activity can be determined as described in Example 1.

According to the invention, the isomaltulose synthase of EC 5.4.99.11 can be present in any conceivable form in the granules according to the invention, thus, for example, in the form of whole cells, disrupted cells, cell extracts or purified.

It is preferred according to the invention that the isomaltulose synthase is present in the form of whole-cell catalysts.

It is alternatively preferred according to the invention that the isomaltulose synthase is present in the form of disrupted cells.

Suitable whole-cell catalysts are described for example in EP 0625578 as *Protaminobacter rubrum* (in particular CBS 574.77), *Serratia plymuthica* (in particular ATCC 15928), *Serratia marescens* (in particular NCIB 8285), *Leuconostoc mesenteroides* (in particular NRRL-B 512 F, in particular ATCC 1083 a) and *Erwinia rhapontici* (in particular NCPPB 1578), in
EP 0392556 and EP1257638 as *Klebsiella terrigena* JCM 1687, *Klebsiella* sp. No. 88 (FERM BP-2838) and *Kiebsiella singaporiensis* LX3 and LX21 and in
EP1328647 as *Pantoea disperse* UQ68J.

The granules according to the invention comprise at least one polymer selected from $C_1$-$C_{10}$-alkyl acrylate polymer, $C_1$-$C_{10}$-alkyl methacrylate polymer and $C_1$-$C_{10}$-alkyl acrylate-$C_1$-$C_{10}$-alkyl methacrylate copolymer, where the aforementioned groups of substances can be covered by the nomenclature "$C_1$-$C_{10}$-alkyl (meth)acrylate (co)polymer". The polymer present preferably exerts a function as binder in the granules according to the invention.

Granules preferred according to the invention are characterized in that the polymer has a mass-average molecular weight of about 100 000 to 1 500 000 g/mol, preferably 500 000 to 1 000 000 g/mol.

The mass-average molecular weight is determined by means of gel permeation chromatography (GPC). The samples were characterized in tetrahydrofuran as eluent and against polystyrene as standard in accordance with DIN 55672-1.

In preferably present alkyl (meth)acrylate polymers and copolymers, the alkyl group has 1 to 4 carbon atoms.

Preferably, the granules according to the invention comprise, as polymer, at least one $C_1$-$C_{10}$-alkyl acrylate-$C_1$-$C_{10}$-alkyl methacrylate copolymer.

Granules particularly preferred according to the invention are characterized in that the polymer is an ethyl acrylate/methyl methacrylate copolymer or methyl acrylate/ethyl acrylate copolymer, where ethyl acrylate/methyl methacrylate copolymer, in particular poly(ethyl acrylate-co-methyl methacrylate) 2:1, is particularly preferred.

Ethyl acrylate/methyl methacrylate copolymers are sold for example under the trade name Kollicoat EMM 30D by BASF AG or under the trade name Eudragit NE or Eudragit NM by Evonik Industries.

The granules according to the invention comprise at least one inorganic carrier material. Contemplated as suitable carrier materials are all inorganic carrier materials suitable for producing granules and known to the person skilled in the art. Preferably, these have a hydrophilic surface. Illustrative representatives of such carrier materials are described in Linqiu Cao, 2006; Carrier-bound Immobilized Enzymes: Principles, Application and Design, Chapter 1. Introduction: Immobilized Enzymes: Past, Present and Prospects; Wiley.

Granules preferred according to the invention are characterized in that the inorganic carrier material is selected from silicas, in particular precipitated silicas, and aluminium silicates, in particular zeolites, with precipitated silicas being particularly preferred.

Zeolites that can be used are, for example, zeolite A, zeolite P, zeolite X or mixtures thereof. Suitable zeolites include, for example, commercial products such as Wessalith® (Evonik Industries), Zeolith MAP® (ex Crosfield) or VEGOBOND AX® (ex SASOL).

Suitable silicas are sold for example by Evonik Industries as Aerosil® or Sipernat®, for example Sipernat 320.

Silicas which are suitable as fillers are commercially available under the names Aerosil® or Sipernat® (Evonik Industries).

Granules preferred according to the invention are characterized in that B) is present, based on the total granules, in an amount of from 0.1% by weight to 80% by weight, preferably from 1% by weight to 50% by weight, particularly preferably from 5% by weight to 35% by weight, and C) is present in an amount of from 99.5% by weight to 20% by weight, preferably from 99% by weight to 30% by weight, particularly preferably from 90% by weight to 40% by weight.

Granules preferred according to the invention are characterized in that these have a specific activity of from 1 to 1000 U/g, preferably 5 to 100 U/g, particularly preferably 10 to 40 U/g. The specific activity (U/g) here defines the activity of the sucrose isomerase, based on the main product (isomaltulose in μmol), which is formed by 1 g of granules per minute under defined conditions (40% sucrose (starting material), RT, pH 6, 100 rpm).

A suitable method for measuring the activity is described in Example 2.

The specific activity of the granules can be controlled for example by increasing or lowering the content of isomaltulose synthase in the granules.

The present invention further provides a process for producing granules comprising the process steps
1) provision of at least one isomaltulose synthase of EC 5.4.99.11, at least one polymer selected from $C_1$-$C_{10}$-alkyl acrylate polymer. $C_1$-$C_{10}$-alkyl methacrylate polymer and $C_1$-$C_{10}$-alkyl acrylate-$C_1$-$C_{10}$-alkyl methacrylate copolymer, preferably $C_1$-$C_{10}$-alkyl acrylate-$C_1$-$C_{10}$-alkyl methacrylate copolymer and at least one inorganic carrier material,
2) production of a dough containing the components of process step 1) and
3) granulation of the dough.

In process step 1) of the process according to the invention, preference is given to using the isomaltulose syntheses, polymers and carrier materials which are preferably present in preferred granules according to the invention.

In process step 2) of the process according to the invention, the components are homogenized.

Preferably, the dough in process step 2) comprises, based on the total dough, B) in an amount of from 0.1% by weight to 80% by weight, preferably from 1% by weight to 50% by weight, particularly preferably from 5% by weight to 35% by weight, and C) in an amount of from 99.5% by weight to 20% by weight, preferably from 99% by weight to 30% by weight, particularly preferably from 90% by weight to 40% by weight. Besides the aforementioned constituents, the dough can comprise water in an amount which ensures an adequate homogenization of the constituents forming the dough.

In process step 3), the granulation can in principle take place in any desired manner. For example, the dough and optionally further constituents such as water, buffer, stabilizing metal salts, can be processed to give granules by means of extrusion, mixer granulation, fluidized-bed granulation, pan agglomeration, spray agglomeration, spray granulation or compaction in a manner known per se.

In a preferred embodiment, the granulation in a first step comprises the extrusion of the water-containing dough which comprises the components A), B) and C) and optionally further constituents such as buffers, stabilizing metal salts. Here, water is present in an amount which ensures an adequate consistency (plastification) of the dough for the extrusion.

The amount of water required for this purpose can be ascertained in a manner known per se by a person skilled in the art in the field of enzyme formulation. The water fraction in the dough at the start of the granulation is typically in the range from 10% by weight to 80% by weight, in particular in the range from 15% by weight to 70% by weight and specifically in the range from 20% by weight to 60% by weight, based on the total weight of the dough.

The production of the dough in this preferred embodiment takes place in process step 2) in a manner known per se by mixing the constituents forming the dough in a suitable mixing device, for example in a customary mixer or kneader. For this purpose, the solid or solids, e.g. the carrier material, are intensively mixed with a liquid phase, for example water, an aqueous binder solution or an aqueous enzyme concentrate. As a rule, the carrier will be introduced into the mixer in the form of a solid and mixed with an aqueous enzyme concentrate and also with the polymer, preferably in the form of a separate aqueous solution or dissolved in the aqueous enzyme concentrate, and also optionally with stabilizing salt, preferably in the form of a separate aqueous solution or suspension, in particular dissolved or suspended in the aqueous enzyme concentrate. Optionally, further water will be added to establish the desired consistency of the dough.

Preferably, a temperature of 60° C., in particular of 40° C., will not be exceeded during the mixing. Particularly preferably, the temperature of the dough is 10 to 30° C. during the mixing. Optionally, the mixing device will therefore be cooled during the dough production.

In this preferred embodiment, in process step 3), the dough obtained in this way is then subjected to an extrusion, preferably an extrusion at low pressure. Extrusion, particularly extrusion at low pressure, generally takes place in an apparatus in which the mass to be extruded (dough) is pressed through a die. The hole diameter of the die determines the particle diameter and is generally in the range from 0.3 to 2 mm and in particular in the range from 0.4 to 1.0 mm. Suitable extruders are e.g. dome extruders or basket extruders, which are sold inter alia by companies such as Caleva, Fitzpatrick or Bepex. If the consistency of the mass to be granulated is correct, there is only a slight temperature increase as it passes through the die (up to about 20° C.). Preferably, the extrusion takes place with temperature control, e.g. the temperature of the dough should not exceed a temperature of 70° C., in particular 60° C., during the extrusion. In particular, the temperature of the dough during the extrusion is in the range from 10 to 40° C.

The extruded dough strands leaving the extruder break up into short granule-like particles or can likewise be broken with the help of suitable cutting devices. The granule particles obtained in this way typically have a homogeneous grain size, i.e. a narrow grain size distribution.

Furthermore, it has proven to be advantageous to round, i.e. to spheronize, the still-wet granules before implementing drying. This reduces the formation of undesired dust particles in the end product, in particular.

Devices suitable for the rounding of the wet granules are so-called spheronizers, which essentially have a horizontally rotating disc onto which the extrudates are pressed as a result of the centrifugal force onto the wall. The extrudates break at the micronotches pregiven by the extrusion process, such that cylindrical particles with a ratio of diameter to length of about 1:1.3 to 1:3 are formed. As a result of the mechanical loading in the spheronizer, the initially cylindrical particles become somewhat rounded.

In this way, granules are obtained with a comparatively high water content, which is generally more than 15% by weight, for example in the range from 15 to 50% by weight, in particular in the range from 20 to 45% by weight, based on the total weight of the wet granules. According to the invention, they are therefore preferably dried in a manner such that their water content is not more than 30% by weight and is preferably in the range from 1 to 12% by weight, in particular in the range from 3 to 10% by weight and specifically in the range from 5 to 9% by weight.

The confectioning accordingly generally comprises a drying step. This preferably takes place in a fluidized-bed drier. Here, a preferably heated gas, as a rule air or a stream of nitrogen, is passed through the product layer from below. The amount of gas is usually adjusted such that the particles are fluidized and swirl. As a result of the gas/particle heat transition, the water is evaporated. Since enzyme-containing granules are generally temperature-labile, it is ensured that the temperature of the granules does not increase too much, i.e. as a rule not over 80° C. and preferably not over 70° C. In particular, the temperature of the granules during drying is in the range from 10 to 40° C. The drying temperature can be controlled in a simple manner via the temperature of the gas stream. The temperature of the gas stream is typically in the range from 140 to 40° C. and in particular in the range from 120 to 60° C. The drying can take place continuously or discontinuously.

After the drying, the granules can also be fractionated by means of a sieve. Coarse material and fines can be ground and returned to the mixer for the purposes of mashing up the granulating mass.

The present invention is described in exemplary fashion in the examples cited below, without the invention, the scope of application of which results from the whole of the description and the claims, being limited to the embodiments mentioned in the examples.

The following figures are a component of the examples:

FIG. 1: Specific activity (U/g) based on the main product (isomaltulose in μmol) which is formed per minute under defined conditions (40% sucrose (starting material), RT, pH 6, 100 rpm), by 1 g of granules or by a fermentation liquor comprising P. rubrum with a biomass equivalent to the granules.

Figure 2:
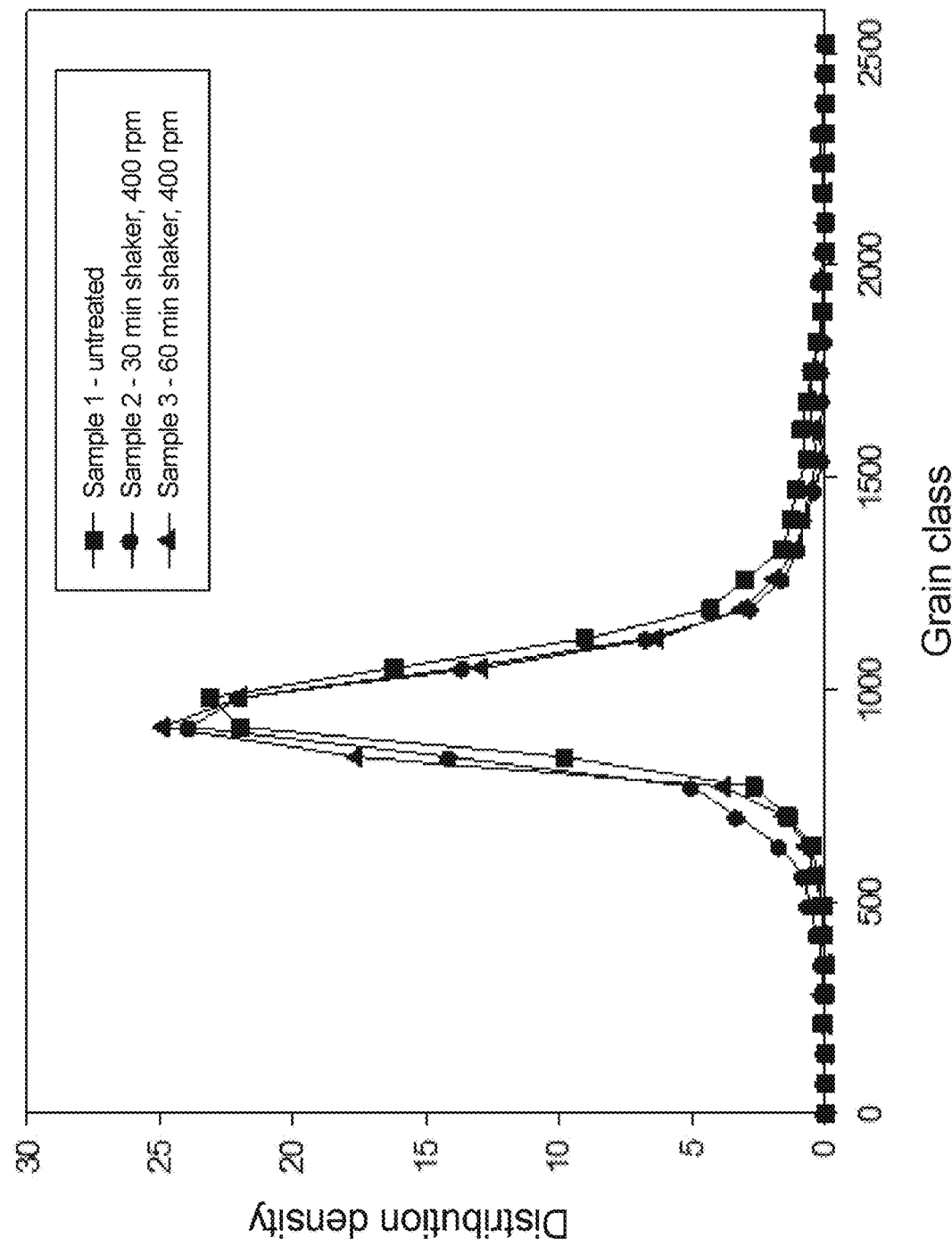

FIG. 2: Graph of the particle size distribution of the preparation according to the invention (untreated or after incubation on a shaker at 400 rpm) as a function of distribution density.

Figure 3:
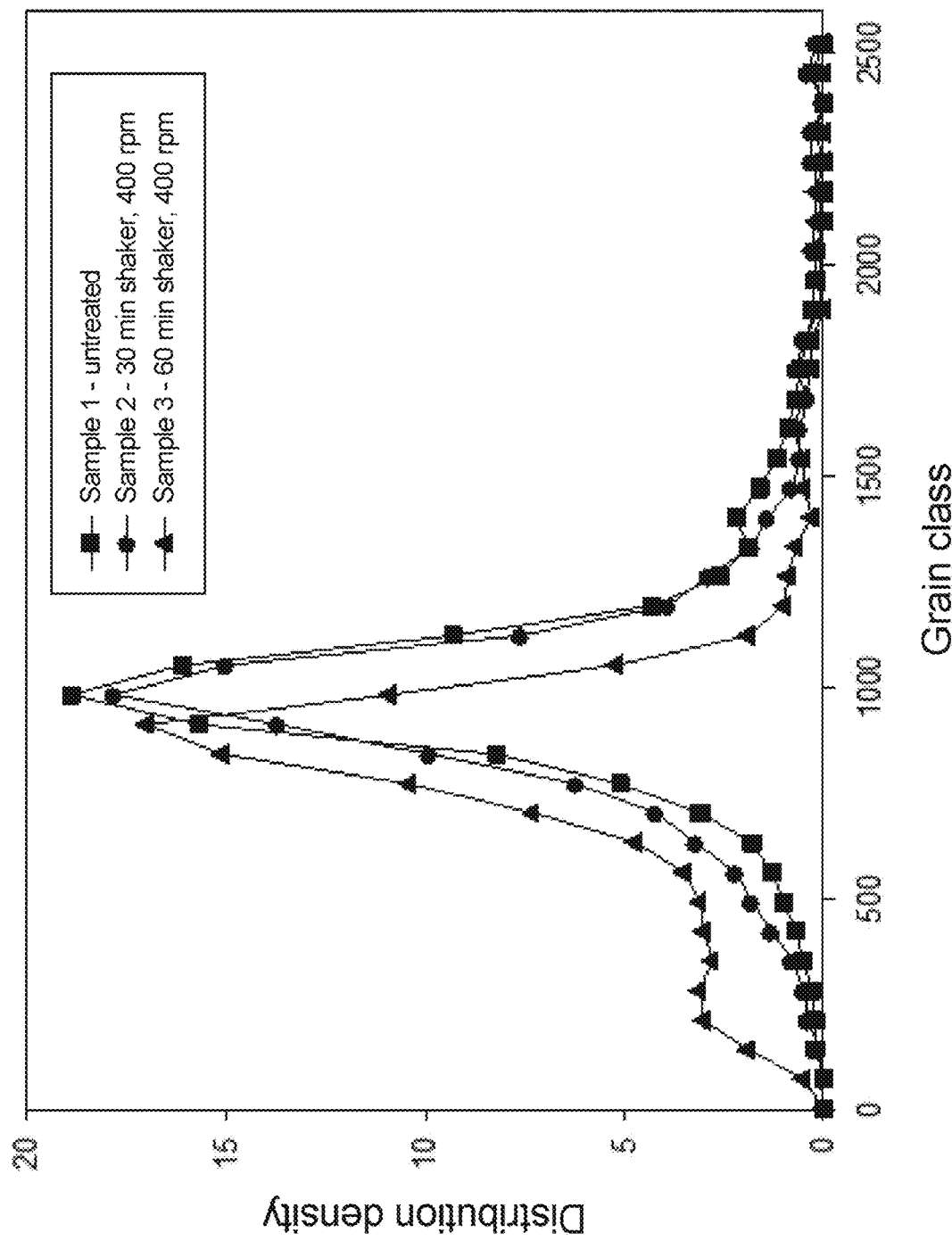

FIG. 3: Graph of the particle size distribution of the non-inventive preparation (untreated or after incubation on a shaker at 400 rpm) as a function of distribution density.

Figure 4:
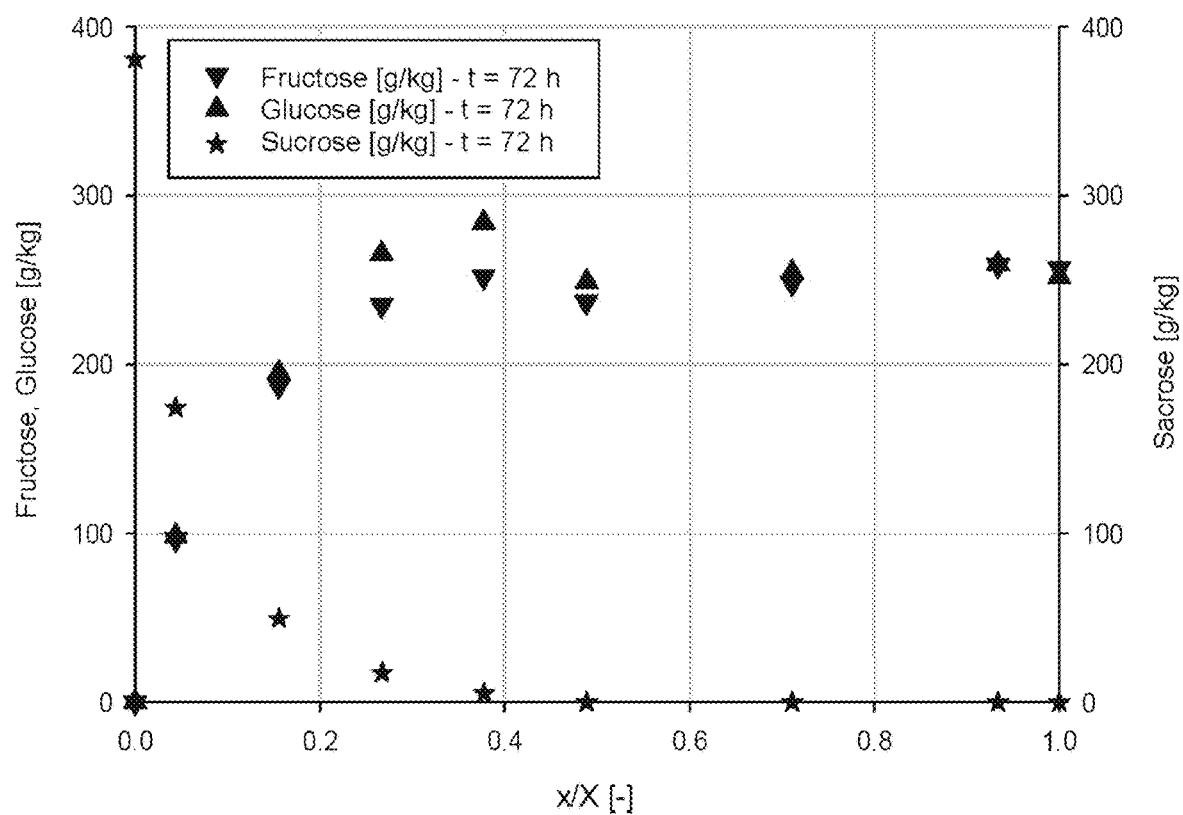

FIG. 4: Graph of the conversion of sucrose into fructose and glucose.

EXAMPLES

Example 1

Production of a Preparation According to the Invention 100 ml of a 30% strength by weight dispersion of an ethyl acrylate/methyl methacrylate copolymer (Eudragit NM, Evonik Industries AG) are homogenized with 130 ml of dry mass 6% by weight strength fermentation liquor of P. rubrum and 62 g of carrier material consisting of Sipernat 320 (Evonik Industries AG) in a kneader. The homogeneous mixture is then extruded using an extruder (Extruder 20, Caleva) and granulated using a spheronizer (Spheronizer 250, Cavela).

The resulting granules are dried overnight at room temperature and a residual moisture of 30% (w/w) is adjusted, ascertained by dry weighing.

Based on total dry weight, the particles comprise 30% by weight of ethyl acrylate/methyl methacrylate copolymer, 8% by weight of fermentation dry mass and 62% by weight of sipernat.

Example 2

Apparent Activity

Determination of the apparent activity of the preparation according to Example 1.

The determination of the activity takes place in three separate batch mixtures. For this, in each case 1 g of the dried granules is placed into a 15 ml reaction tube and supplied with 10 ml of 40% (w/w) sucrose solution. Incubation takes place on a shaker with 100 rpm at RT and a pH of 6. The specific activity U/g was ascertained after an incubation time of 120 min by determining the product concentration. This was ascertained here in each case with the help of HPLC analysis. The specific activity of fermentation liquor containing P. rubrum was determined analogously, with a biomass equivalent to the granules present.

The results are shown in FIG. 1.

Example 3

Mechanical Stability

The mechanical stability of the preparation according to Example 1 is assessed by means of the determination of the d10 [μm], d50 [μm] and the d90 [μm] value of the particle size distribution from the distribution density function. This was determined visually under standard conditions with the help of a Retsch Camsizer.

The determination of the particle size distribution takes place untreated and also after incubation for 30 and 60 minutes in a 50 ml reaction vessel with in each case 25 g of granules and 25 g of medium on a shaker (400 rpm) in the medium and subsequent drying. It is clear, particularly as a result of the virtually unchanged dl 0 [μm] value, which is to be deduced from the distribution density function, that the preparation is stable and no particle fragments are formed. Accordingly, 10% of the particles of the particle collective prior to incubation have a diameter of less than 881 μm and, after incubation for 60 minutes, a diameter of less than 866 μm.

Particle Size Distribution—Preparation According to the Invention

| Preparation according to the invention | | d(10) [μm] | d(50) [μm] | d(90) [μm] |
|---|---|---|---|---|
| Sample 1 | In medium - 0 min | 881 | 1017 | 1267 |
| Sample 2 | In medium - 30 min shaker, 400 rpm | 818 | 980 | 1160 |
| Sample 3 | In medium - 60 min shaker, 400 rpm | 866 | 983 | 1183 |

Example 4

Production of a Preparation According to the Invention Comprising *Saccharomyces cerevisiae* with the Enzyme Invertase (EC 3.2.1.26)

The production of the preparation takes place as in Example 1, except that the biocatalytic active component used is 130 ml of a dry mass 6% by weight strength suspension comprising standard commercial *Saccharomyces cerevisiae*. The *Saccharomyces cerevisiae* whole cells contain inter alia the enzyme invertase (EC 3.2.1.26) from the group of hydrolases of EC 3, which hydrolytically cleaves sucrose into fructose and glucose. To investigate the apparent activity, the preparation was placed into a fixed-bed reactor which has side septums for sampling. The starting material used was a 40% (w/w) sucrose solution which was adjusted to a pH of 6. The starting material was fed in at an LHSV [h−1] of 0.2, which is formed by the quotient of volume stream [m3/h] and the catalyst volume used [m3]. In order to achieve a steady state in the fixed-bed reactor, sampling was carried out after a run-in phase of 72 h. Since sampling was carried out along the length of the reactor, the conversion of the starting material can be monitored over the dimensionless reactor length x/X [−]. The sample composition was ascertained in each case with the help of HPLC analysis. The results are shown in FIG. 4.

Comparative Example 1 (not According to the Invention)

Production of a Preparation not According to the Invention

Production of a preparation according to WO95/22606 (Novo Nordisk NS): Method for production of an immobilized enzyme preparation and use of the immobilized enzyme preparation.

65 g of Celkate T-21 are added in powder form to a high-speed mixer. To this, 25 g of liquid fermentation liquor comprising sucrose isomerase are added to the powder continuously and with running impellor. Then, a further 50 g of liquid fermentation liquor comprising sucrose isomerase, combined with 3% (w/w) Kollidon K25 polyvinylpyrrolidone (BASF) are added. The resulting granules are dried overnight at room temperature and sieved. The residual moisture content is adjusted to 10%.

Comparative Example 2 (not According to the Invention)

Mechanical Stability

Determination of the mechanical stability of the preparation according to Comparative example 1. The measurement was carried out analogously to Example 1. Results are shown in FIG. 3. The considerable shift in the d10 value [μm] shows that before the incubation 10% of the particle collective is less than 784 μm and after incubation less than 389 μm. This means that the preparation not according to the invention disintegrates into smaller particle fragments as a result of the mechanical stress on the shaker.

| Preparation not according to the invention | | d(10) [μm] | d(50) [μm] | d(90) [μm] |
|---|---|---|---|---|
| Sample 1 | In medium - 0 min | 784 | 1024 | 1355 |
| Sample 2 | In medium - 30 min shaker, 400 rpm | 695 | 1004 | 1290 |
| Sample 3 | In medium - 60 min shaker, 400 rpm | 389 | 874 | 1092 |

The invention claimed is:

1. Granules comprising:
   A) at least one isomaltulose synthase of EC 5.4.99.11,
   B) at least one polymer selected from the group consisting of a $C_1$-$C_{10}$-alkyl acrylate polymer, a $C_1$-$C_{10}$-alkyl methacrylate polymer, and a $C_1$-$C_{10}$-alkyl acrylate-$C_1$-$C_{10}$-alkyl methacrylate copolymer, and
   C) at least one inorganic carrier material.

2. The granules according to claim 1, wherein the isomaltulose synthase is present in the form of whole-cell catalysts or in the form of disrupted cells.

3. The granules according to claim 1, wherein the polymer has a mass-average molecular weight of 100000 to 1500000 g/mol.

4. The granules according to claim 1, wherein the polymer is an ethyl acrylate/methyl methacrylate copolymer.

5. The granules according to claim 1, wherein the inorganic carrier material is at least one selected from the group consisting of silicas and aluminum silicates.

6. The granules according to claim 1, wherein, based on the total weight of the granules,
   the at least one polymer B) is present in an amount of from 0.1% by weight to 80% by weight and
   the at least one inorganic carrier material C) is present in an amount of from 20% by weight to 95% by weight.

7. The granules according to claim 1, wherein the granules have a specific activity of 1 to 1000 U, based on the total weight of the granules.

8. The granules according to claim 1, wherein the at least one polymer is a $C_1$-$C_{10}$-alkyl acrylate-$C_1$-$C_{10}$-alkyl methacrylate copolymer.

9. The granules according to claim 1, wherein the polymer has a mass-average molecular weight of 500000 to 1000000 g/mol.

10. The granules according to claim 4, wherein the ethyl acrylate/methyl methacrylate copolymer is poly(ethyl acrylate-co-methyl methacrylate) 2:1.

11. The granules according to claim 5, wherein the silica is a precipitated silica.

12. The granules according to claim 5, wherein the aluminum silicate is a zeolite.

13. The granules according to claim 1, which have a half-value particle size (d50) of 100 to 2000 μm.

14. The granules according to claim 1, which have a d10 value of greater than or equal to 50% of a half-value particle size (d50), a d90 value of less than or equal to 150% of the half-value particle size (d50), or both.

15. The granules according to claim 1, wherein at least one selected from the group consisting of a d10 value, a half-value particle size (d50), and a d90 value is reduced by less than 10% after 60 minutes shaking at 400 rpm in a medium, relative to a d10 value, a half-value particle size (d50), and a d90 value of the granules prior to the shaking.

* * * * *